United States Patent [19]

Müller et al.

[11] Patent Number: 5,118,290

[45] Date of Patent: Jun. 2, 1992

[54] PROCESS FOR PREPARATION OF DENTAL IMPRESSIONS

[75] Inventors: Hanns P. Müller, Odenthal-Blecher; Peter Schwabe, Normagen, both of Fed. Rep. of Germany

[73] Assignee: Bayer Aktiengesellschaft, Leverkusen, Fed. Rep. of Germany

[21] Appl. No.: 304,395

[22] Filed: Jan. 30, 1989

Related U.S. Application Data

[62] Division of Ser. No. 109,343, Oct. 15, 1987, abandoned.

[30] Foreign Application Priority Data

Oct. 30, 1986 [DE] Fed. Rep. of Germany ....... 3636974

[51] Int. Cl.$^5$ ............................................. A61C 1/00
[52] U.S. Cl. ........................................ 433/48; 433/214
[58] Field of Search .............................. 433/488, 214

[56] References Cited

U.S. PATENT DOCUMENTS

| | | | |
|---|---|---|---|
| 3,632,557 | 1/1972 | Brode et al. | 528/28 |
| 4,374,237 | 2/1983 | Berger et al. | 528/28 |
| 4,474,933 | 10/1984 | Huber et al. | 528/22 |
| 4,555,561 | 11/1985 | Sugimori et al. | 528/28 |
| 4,645,416 | 2/1987 | Pohl et al. | 528/28 |
| 4,687,533 | 8/1987 | Rizk et al. | 528/28 |
| 5,066,231 | 11/1991 | Oxman et al. | 528/28 |

FOREIGN PATENT DOCUMENTS 0096249 12/1983 European Pat. Off. .
0158893 10/1985 European Pat. Off. .
0827508 5/1981 U.S.S.R. .

*Primary Examiner*—V. Millin
*Attorney, Agent, or Firm*—Sprung, Horn, Kramer & Woods

[57] ABSTRACT

A process for the preparation of a dental impression comprising

A) forming a mixture of a polyaddition product which contains ether, urethane and urea groups, B) mixing therewith water of proton donor-containing aqueous solution in a weight ratio of A:B of from 1:0.01 to 1:40 and in at least catalytically active amount, the weight ratio of water plus proton donor to the balance of the composition exclusive of the filler ranging from about 0.01:1 to 1:1, and C) applying the mixture formed in B intraorally to a patient to make a negative copy of the patient's teeth.

2 Claims, No Drawings

PROCESS FOR PREPARATION OF DENTAL IMPRESSIONS

This is a division of application Ser. No. 109,343, filed Oct. 15, 1987, now abandoned.

The present invention relates to polyaddition products which contain ether, urethane and urea groups and have alkoxysilyl end groups, a process for their preparation, a mixture containing the polyaddition products and a crosslinking agent and their use of the preparation of dimensionally stable impression or duplicating composition, which are used, in particular, in the dental field.

The polyaddition products can be used, in particular, in the form of pastes, to produce precise impression of gypsum models, jaws with teeth, jaws with some teeth or jaws with no teeth. The mixture used for this purpose consists of a multi-component system which is obtained by mixing the polyadduct containing a crosslinking agent with a catalyst component and water. This mixture crosslinks rapidly at room temperature or body temperature and thereby forms the impression.

Impression compositions which are used in the dental field are known per se (compare, for example, R. G. Craig, Restorative Dental Materials, The C. V. MoosbeComp. St. Louis, Toronto, London, 1980, page 1979 et seq.). Overall, very high requirements are imposed on such materials. They must:

1. be pleasant smelling and tasting and aesthetic appearance;
2. contain no toxic or irritating constituents;
3. have a good storage stability;
4. economical to prepare and give precise impressions;
5. be easy to handle without great technical effort;
6. exhibit hardening characteristics that meet clinical requirements;
7. be elastic and not show residual deformation under tensile stress when hardened
8. have an adequate compressive strength and not break when hardened
9. be dimensionally stable at room temperature under normal atmospheric humidity long enough to prepare exact gypsum impressions in a suitable period of time in the laboratory when hardened
10. cause no gypsum damage and be compatible with other impression materials when hardened.

The impression compositions of the prior art do not meet all of the abovementioned requirements. Thus, alignate impression compositions shrink due to rapid evaporation of the water and become brittle.

Polysulphide impression compositions are dark-colored and contain compounds of lead or copper as accelerators.

Polyether impression compositions contain ethyleneimine crosslinking agents, polysiloxane impression compositions, and, because of their hydrophobic character, occasionally give defective impressions due to moisture in the oral cavity.

The present invention therefore seeks to avoid the disadvantages of the known impression compositions and moreover provide crosslinkable polyaddition products which, in addition to being physiologically acceptable, also meet all of the other requirements listed above.

The present invention thus relates to polyaddition products which contain ether, urethane and urea groups and have alkoxysilyl end groups and a predominantly linear molecular structure with exclusively aliphatically or cycloaliphatically bonded ether, urethane and urea segments and an average molecular weight $M_n$ of 800–20,000. These polyaddition products according to the present invention contain a) 25 to 90 parts by weight, preferably 50 to 80 parts by weight, of polyether groups per 100 parts by weight of polyaddition product, b) 0.5 to 10 parts by weight, preferably 1 to 8 parts by weight, of urethane groups

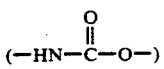

per 100 parts by weight of polyaddition product, c) 0.5 to 10 parts by weight, preferably 1–8 parts by weight, of urea groups

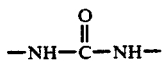

per 100 parts by weight of polyaddition product and d) 1 to 25 parts by weight, preferably 2 to 10 parts by weight, of terminal alkoxysilyl groups

per 100 parts by weight of polyaddition product. The alkoxysilyl groups in the polyadduct are introduced via compounds having the following formula:

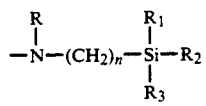

wherein n represents a number from 1 to 6, preferably the number 3,

R denotes hydrogen or $-(CH_2)_n-SiR_1R_2R_3$, $R_1$ denotes $C_1-C_4$-alkoxy, preferably methoxy or ethoxy, and $R_2$ and $R_3$ have the same meaning as $R_1$ and additionally represent the methyl or ethyl group.

The polyaddition products according to the invention can be prepared by a process in which aliphatic and/or cycloaliphatic diisocyanates are reacted with dihydroxypolyethers with an average molecular weight range $M_n$ of 300 to 6,000. If appropriate aliphatic and/or cycloaliphatic dihydric alcohols with an average molecular weight $M_n$ of 62 to <300 can also be added, and the resulting prepolymers then reacted with alkoxysilyl monoamines. It is also possible, if appropriate, for aliphatic and/or cycloaliphatic diamines with primary amino groups and with a molecular weight $M_n$ of 60 to 300 to be used. The process is characterized in that a) alkoxysilylmonoamines of the formula

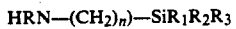

with the meanings described in more detail above, b) per 1 part by weight of dihydroxypolyether, 0.05 to 1.5, preferably 0.1 to 0.5, parts by weight of the diisocyanate, 0 to 0.6, preferably 0 to 0.2, part by weight of the dihydric alcohol, 0.02 to 0.40, preferably 0.05 to 0.2, part by weight of the alkoxysilylmonoamine and 0 to 0.6, preferably 0 to 0.2, part by weight of the diamine are employed.

The components are reacted at temperatures of 20° to 150° C., preferably 60° to 120° C.

The diamines which are employed serve to establish the particular molecular weight desired.

Suitable diisocyanates are, in particular, those with aliphatically and/or cycloaliphatically bonded isocyanate groups of the formula $Q(NCO)_2$, in which a Q represents an aliphatic hydrocarbon radical with 2 to 12 carbon atoms or a cycloaliphatic or mixed aliphatic-cycloaliphatic hydrocarbon radical with 4 to 15 carbon atoms.

Examples of such diisocyanates are ethylene diisocyanate, tetramethylene diisocyanate, hexamethylene diisocyanate, dodecamethylene diisocyanate, cyclobutane 1,3-diisocyanate, cyclohexane 1,3- and 1,4-diisocyanate or 1-isocyanato-3,3,3-trimethyl-5-isocyanatomethyl-cyclohexane, and any desired mixtures of such diisocyanates. Cycloaliphatic or mixed aliphatic-cycloaliphatic diisocyanates are preferably employed in the process according to the invention. 1-Isocyanato-3,3,5-trimethyl-5-isocyanato-methyl-cyclohexane (isophorone diisocyanate) is particularly preferred.

Suitable dihydroxypolyethers are likewise those which are known per se and are prepared, for example, by polymerization of epoxides, such as ethylene oxide, propylene oxide, butylene oxide, tetrahydrofuran, styrene oxide or epichlorohydrin, by themselves, for example in the presence of $BF_3$, or by addition of these epoxides, if appropriate, as a mixture or in succession, onto starting components with reactive hydrogen atoms, such as alcohols or amines, for example water, ethylene glycol, propylene 1,3-glycol or 1,2-glycol, 4,4'-dihydroxydiphenylpropane or aniline. Those polyethers which contain predominantly primary OH groups (up to 90% by weight, based on all the OH groups present in the polyether) are frequently preferred.

Suitable diamines are, preferably, aliphatic, cycloaliphatic or mixed aliphatic-cycloaliphatic diamines in the molecular weight range 60 to 300, which contain primary amino groups. Examples are ethylenediamine, tetramethylenediamine, hexamethylenediamine, 4,4'-diamino-dicyclohexylmethane, 1,4-diaminocyclohexane, 4,4'-diamino-3,3'-dimethyl-dicyclohexylmethane and 1-amino-3,3,5-trimethyl-5-aminoethyl-cyclohexane (isophoronediamine). 4,4'-Diaminodicyclohexylmethane or 1-amino-3,3,5-trimethyl-5-aminomethyl-cyclohexane (isophoronediamine) the isophoronediamine are especially preferred.

Possible dihydric alcohols are, for example, ethylene glycol, propylene 1,2-glycol and 1,3-glycol, butylene 1,4-glycol and 2,3-glycol, hexane-1,6-diol, octane-1,8-diol, neopentylglycol, cyclohexanedimethanol, 1,4-bis-hydroxymethyl-cyclohexane, 2-methyl-1,3-propanediol, 3-methylpentane-1,5-diol, and furthermore diethylene glycol, triethylene glycol, tetraethylene glycol polyethylene glycols, dipropylene glycol, polypropylene glycols, dibutylene glycols and polybutylene glycols.

Suitable monoamines are likewise known, and these are preferably the $\gamma$-aminopropyl-tri-$C_1$-$C_4$-alkoxysilanes which are readily available industrially, or bis-(3-$C_1$-$C_4$-alkoxysilylpropyl)-amines. $\gamma$-aminopropyl-triethoxysilane is especially preferred.

The invention furthermore relates to a mixture of the polyaddition product as previously described with a crosslinking agent, and silicic acid tetra-esters, in particular tetraethoxysilane. Polyalkoxypolysiloxanes are preferably used as the crosslinking agent.

0.01 to 5, preferably 0.1 to 1, parts by weight of the crosslinking agent can be employed per part by weight of the polyaddition product.

This mixture is prepared in a manner which is known to the expert, for example, by mixing the components at room temperature, or, if appropriate, at a moderately elevated temperature, e.g., up to 60° C.

For use of the polyaddition product according to the invention for dental purposes, it is advisable also to add a catalyst and water to the mixture consisting of polyaddition product and crosslinking agent so that crosslinking is accelerated. Specifically, impression compositions which are used in the oral cavity of a patient should harden rapidly to a dimensionally stable form.

The invention thus furthermore relates to mixtures of A, i.e., the mixture described above of the polyaddition product according to the invention with a crosslinking agent, and B, water and proton donors, in weight ratios of 1:0.01 to 1:40, preferably 1:0.05 to 1:1, it being necessary for component B to be present in the mixture in at least catalytic amounts.

More preferably the amount of component B should not exceed 40% by weight, with any amounts of fillers also used not being taken into consideration.

Both component A and component B can contain other customary auxiliaries and/or additives.

Auxiliaries and/or additives are understood as, for example, paraffins, emulsifiers, glycerol, sorbitol and fillers, for example quartz-cristobalite powders, calcium sulphate, diatomaceous earth, silicates and filled and pyrogenically produced silicon dioxide with a charged or uncharged surface.

Dyestuffs can be used to differentiate component A from component B, so that no confusion occurs during mixing.

It is furthermore advantageous to use indicators, for example bromophenol blue, as a mixing control. Such indicators indicate when the mixing of components A and B can be ended. The end is indicated by a change in color.

Proton donors are understood as organic and/or inorganic acids, such as acid ion exchangers, phosphoric acid, dibutylphosphoric acid, dilute sulphuric acid, tartaric acid, citric acid, adipic acid and the like. Tartaric acid is preferred.

The ready-to-use impression composition then hardens—depending on the formulation and the ambient temperature—within the period customary during use—to an elastic material which reproduces every detail accurately.

Gypsum models or impressions, using commercially available impression compositions, can be produced rom the hardened material.

It is to be regarded as exceptionally surprising that the formulations according to the invention give impression compositions which, when retaking impressions, for example with gypsum, cause no gypsum damage, and that the hardened compositions, although they contain water, remain dimensionally stable over a longer period than, for comparison, hydrocolloids.

The compositions according to the invention are furthermore distinguished in that they harden without metals and the crosslinked mixture is readily wetted by any moisture available.

The following composition of component A may be mentioned as an example:

100 parts by weight of component A containing a) 20-50 parts by weight of polyaddition product according to the invention, b) 5-30 parts by weight of tetraethoxysilane, c) 0-15 parts by weight of paraffins, d) 0-70 parts by weight of fillers, e) 0-5 parts by weight of emulsifier and f)0.01 part by weight of indicator. The following composition of component B may be mentioned as an example:

100 parts by weight of component B contain g) 5-30 parts by weight of organic or inorganic acids, h) 0.1-10 parts by weight of water, i) 0-10 parts by weight of emulsifier, k) 0-10 parts by weight of glycerol, l) 0-70 parts by weight of fillers and m) 0-10 parts by weight of paraffins.

The following examples serve to illustrate the invention further.

EXAMPLES

Example 1

800 g (0.4 mol of OH) of a linear polyether of MW 4000 (prepared by polyaddition of 87 parts by weight of propylene oxide onto propylene glycol and subsequent polyaddition of 13 parts by weight of ethylene oxide) are dehydrated at 120° C. under a waterpump vacuum for 30 minutes. Thereafter, 88.8 g (0.8 mol of NCO) of isophorone diisocyanate (called IPDI below) are added to the batch and the entire mixture is stirred at 120° to 140° C. under nitrogen for 4 hours. The NCO number of the prepolymer is then determined:
NCO found: 1.70%.
NCO calculated: 1.89%.

88.4 g (0.4 mol) of 3-aminopropyltriethoxysilane are then added dropwise to the prepolymer at 30° C. in the course of 30 minutes, with stirring and under nitrogen. The mixture warms to 50° C. It is then allowed to after-react at 60° C. for 30 minutes. No further NCO can be detected in the resulting polyurethane-polyurea by IR spectroscopy. After cooling, an almost colorless, clear, viscous product with a content of —HN—CO—NH— of 1.237% by weight and a content of terminal alkoxysilyl groups of 6.22% by weight is obtained in this manner.

Example 2

1,000 g (0.5 mol of OH) of a linear polyether of MW 4000 (prepared by polyaddition of 70 parts by weight of propylene oxide onto propylene glycol and subsequent polyaddition of 30 parts by weight of ethylene oxide) are dehydrated as in Example 1. 111 g (1 mol of NCO) of IPDI are added to the batch at 40° C. in one operation, followed by 1 drop of tin octoate. The batch is heated to 110° C., with stirring and under nitrogen, and is left at this temperature for 40 minutes. The NCO number of the prepolymer is then determined:
NCO found: 1.69%
NCO calculated: 1.89%.

After cooling to 60° C., 110.5 g (0.5 mol) of 3-aminopropyl-triethoxysilane are added dropwise in the course of 10 minutes, with stirring and under nitrogen. The batch warms to 75° C. It is allowed to after-react for 30 minutes without further heating. No further free NCO is detectable in the resulting polyurethane-polyurea by IR spectroscopy. The polyurethane-polyurea is colorless and clear, can easily be poured and has a content of —NH—CO—NH— of 2.37% by weight and a content of terminal alkoxysilyl groups of 6.22% by weight.

Example 3

1,000 g (1 mol of OH) of a linear polyether of MW 2000 (prepared by polyaddition of equal parts by weight of propylene oxide and ethylene oxide onto propylene glycol) are dehydrated as in Example 1. 166.5 g (1.5 mol of NCO) of IPDI are added to the batch in one operation at 80° C., followed by 1 drop of in octoate. The batch is stirred at 120° C. for 4 hours under nitrogen. The NCO number of the prepolymer is then determined:
NCO found: 1.79%.
NCO calculated: 1.80%.

After cooling to 60° C., 110.5 g (0.5 mol) of 3-aminopropyl-triethoxysilane are then added, with stirring and under nitrogen. Thereafter, the batch is free of NCO. The polyurethane-polyurea is a colorless, clear, highly viscous liquid with a content of —NH—CO—NH— of 2.27% by weight and a content of terminal alkoxysilyl groups of 5.95% by weight.

Example 4

The procedure is as described in Example 3, but with the difference that 639 g of tetraethoxysilane are added to the resulting polyurethane-polyurea after preparation. The homogeneous mixture is clear and colorless and has a viscosity $\eta_{25°\ C.}$ of 2,016 mPas.

The ready-to-use mixture contains 1.51% by weight of —NH—CO—NH— and 3.96% by weight terminally bonded alkoxysilyl groups, and additionally 50% by weight of tetraethoxysilane.

Example 5

An impression composition according to the invention is prepared as follows in a planetary mixer using the polyurethane-polyurea described in Example 3:

Component A 30 parts by weight of polyurethane-polyurea from Example 3, 15 parts by weight of tetraethoxysilane, 11 parts by weight of paraffin, 41 parts by weight of filler, 2.99 parts by weight of emulsifier and 0.01 part by weight of indicator are mixed in the sequence shown. The mixing time at 25° C. is 30 minutes at 50 revolutions/minute.

Component B 25 parts by weight of 15% strength tartaric acid, 4 parts by weight of water, 10 parts by weight of emulsifier, 3 parts by weight of glycerol, 4 parts by weight of paraffin and 54 parts by weight of fillers are mixed in the sequence shown. The mixing time at 25° C. is 30 minutes at 50 revolutions/minute.

Equal parts by weight of components A and B are mixed intensively and crosslinked to an elastic material within 3 minutes.

The physical values of the material, measured in accordance with ISO 4823, are as follows:
Processing time: 2.5 minutes
Consistency: 45 mm
Residual deformation: 2.3%.

The change in dimension, measured in accordance with ADA 19 on dry storage, is:
after 6 minutes: 0.6%
after 10 minutes: 1.1% after 120 minutes: 2.2%.

The elastic deformation, measured in accordance with ADA 19, is 9%.

For comparison

The change in dimension of a hydrocolloid impression composition cannot be measured on dry storage since this dries out too rapidly and, under shrinkage, becomes brittle.

Example 6

An impression composition according to the invention is prepared as follows in a planetary mixer using the polyurethane-polyurea described in Example 3:

Component A 50 parts by weight of polyurethane-polyurea from Example 2, 2 parts by weight of Aerosil ($SiO_2$), 43 parts by weight of filler (quartz powder), 5 parts by weight of emulsifier and 0.05 parts by weight of indicator (bromophenol blue) are mixed in the sequence shown. The mixing time at 25° C. is 30 minutes at 50 revolutions/minute.

Component B 3 parts by weight of 1M HCl in water, 12 parts by weight of emulsifier, 17 parts by weight of glycerol, 10 parts by weight of paraffin (petroleum jelly), 55 parts by weight of fillers (quartz powder) and 3 parts by weight of Aerosil ($SiO_2$) are mixed in the sequence shown. The mixing time at 25° C. is 30 minutes at 50 revolutions/minute.

Equal parts by weight of components A and B are mixed intensively and crosslinked to an elastic material within 5 minutes.

The physical values of the material, measured in accordance with ISO 4823, are as follows:
Processing time: 4 minutes
Residual deformation: 1.1%.
Compatibility with gypsum: no changes
The change in dimension, measured in accordance with ADA 19 on dry storage, is: after 24 hours: 0.2%.

It will be understood that the specification and examples are illustrative but not limitative of the present invention and that other embodiments within the spirit and scope of the invention will suggest themselves to those skilled in the art.

We claim:

1. A process for the preparation of a dental impression comprising
    A) forming a mixture of a polyaddition product which contains ether, urethane and urea groups, said polyaddition product having alkoxysilyl end groups with predominantly linear molecular structure and with exclusively aliphatically or cycloaliphatically bonded ether, urethane and urea segments and an average molecular weight $M_n$ of 800-20,000, the polyaddition product being produced by reacting 0.15-1.5 parts by weight of an aliphatic diiscyanate, a cycloaliphatic diisocyanate or a mixture thereof with 1 part by weight of a dihydroxypolyether with an average molecular weight range $M_n$ of 300-6,000 and 0-0.06 parts by weight of an aliphatic dihydric alcohol, a cycloaliphatic dihydric alcohol with an average molecular weight $M_n$ of 62-300 or a mixture thereof and reacting the resulting prepolymer with 0.02-0.4 parts by weight of an alkoxysilyl monoamine and 0-0.4 parts by weight of an aliphatic diamine with primary amino group and with a molecular weight $M_n$ of 60-300 or a mixture thereof,
        a) the alkoxysilylmonoamine having the formula $HRN-(CH_2)-SiR_1R_2R_3$ wherein
            n represents a number from 1-6
            R denotes hydrogen or 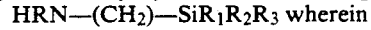—$(CH_2)$—$SiR_1R_2R_3$
            $R^1$ denotes $C_1$-$C_4$ alkoxy, and
            $R^2$ and $R_3$ independently denote $C_1$-$C_4$ alkoxy, methyl or ethyl, and
        b) per 1 part by weight of the dihydroxypolyether there being employed 0.5-1.5 parts by weight of the diiscyanate, 0.6 parts by weight of the dihydric alcohol, 0.2-0.7 parts by weight of the alkoxysilylmonoamine and 0-0.6 parts by weight of the diamine,
    B) mixing therewith water of a proton donor-containing aqueous solution in a weight ratio of A:B of from 1:0.01 to 1:40 and in at least catalytically active amount, the weight ratio of water plus proton donor to the balance of the composition exclusive of the filler ranging from about 0.01:1 to 1:1, and
    C) applying the mixture formed in B intraorally to a patient to make a negative copy of the patient's teeth.

2. The process according to claim 1, wherein in B the weight ratio of water plus proton donor to the balance of the composition exclusive of the filler ranges from about 0.05:1 to 1:1.

* * * * *

UNITED STATES PATENT AND TRADEMARK OFFICE
CERTIFICATE OF CORRECTION

PATENT NO. : 5,118,290
DATED : June 2, 1992
INVENTOR(S) : Muller et al.

It is certified that error appears in the above-identified patent and that said Letters Patent is hereby corrected as shown below:

Col. 8, line 12   Delete " diiscyanate " and substitute -- diisocyanate --

Col. 8, line 15   Delete " 0-0.06 " and substitute -- 0-0.6 --

Col. 8, line 33   Delete " diicyanate " and substitute -- diisocyanate --

Signed and Sealed this

Fifteenth Day of March, 1994

Attest:

BRUCE LEHMAN

Attesting Officer    Commissioner of Patents and Trademarks